United States Patent
Dittmann et al.

(10) Patent No.: US 6,691,705 B2
(45) Date of Patent: Feb. 17, 2004

(54) ARRANGEMENT AND PROCESS FOR CONTROLLING A NUMERICAL VALUE FOR PATIENT RESPIRATION

(75) Inventors: Ralf Dittmann, Söllbrock (DE); Swen Grünitz-Post, Lägerfeld (DE); Steffen Leonhardt, Lübeck (DE); Andrea Gentilini, Zürich (CH); Adolph Glattfelder, Zürich (CH); Manfred Morari, Zollikon (CH); Thomas Schnider, Büren (CH); Alexander M Zbinden, Bern (CH)

(73) Assignee: Dräger Medizintechnik GmbH, Lübeck (DE)

( * ) Notice: Subject to any disclaimer, the term of this patent is extended or adjusted under 35 U.S.C. 154(b) by 244 days.

(21) Appl. No.: 09/815,092

(22) Filed: Mar. 22, 2001

(65) Prior Publication Data

US 2002/0014236 A1 Feb. 7, 2002

(30) Foreign Application Priority Data

Mar. 25, 2000 (DE) .......................... 100 15 026

(51) Int. Cl.⁷ ............................ A61M 16/00; A61B 5/04
(52) U.S. Cl. ............................ 128/203.25; 128/204.21; 600/544
(58) Field of Search .................. 128/203.12, 203.14, 128/203.25, 204.21, 204.23, 204.22, 204.18; 600/544, 545, 546, 529

(56) References Cited

U.S. PATENT DOCUMENTS

| | | | | |
|---|---|---|---|---|
| 2,888,922 A | * | 6/1959 | Bellville ................. | 128/204.23 |
| 5,094,235 A | | 3/1992 | Westenskow et al. | |
| 5,265,594 A | | 11/1993 | Olsson et al. | |
| 5,320,109 A | * | 6/1994 | Chamoun et al. ........... | 600/544 |
| 5,332,401 A | | 7/1994 | Davey et al. | |
| 5,372,140 A | | 12/1994 | Pomfrett | |
| 5,713,856 A | * | 2/1998 | Eggers et al. ................ | 604/65 |
| 5,931,161 A | * | 8/1999 | Keilbach et al. ........ | 128/204.22 |
| 5,957,885 A | * | 9/1999 | Bollish et al. ................ | 604/67 |
| 6,016,444 A | * | 1/2000 | John ........................... | 600/544 |
| 6,273,855 B1 | | 8/2001 | Schmid et al. | |
| 6,305,373 B1 | * | 10/2001 | Wallace et al. ........ | 128/204.21 |
| 6,317,627 B1 | * | 10/2001 | Wallace et al. ............. | 600/544 |
| 2002/0017299 A1 | * | 2/2002 | Hickle .................... | 128/204.21 |

FOREIGN PATENT DOCUMENTS

| | | |
|---|---|---|
| CA | 1322026 | 9/1993 |
| DE | 3854131 T2 | 3/1996 |
| DE | 69126315 T2 | 10/1997 |
| DE | 19624133 A1 | 12/1997 |
| DE | 69031838 T2 | 7/1998 |
| DE | 4004034 C2 | 5/1999 |
| DE | 19821761 A1 | 11/1999 |
| EP | 0236513 A1 * | 9/1987 |
| EP | 0483401 B1 | 10/1994 |

* cited by examiner

Primary Examiner—Aaron J. Lewis
Assistant Examiner—Teena Mitchell
(74) Attorney, Agent, or Firm—McGlew and Tuttle, P.C.

(57) ABSTRACT

An arrangement with a control circuit for controlling a numerical value for patient respiration as well as to a process for controlling the numerical value. The numerical value is controlled on the basis of an evaluation of the EEG (electroencephalogram) of the patient (1) by an EEG sensor (2), e.g., by determining the so-called BIS (bispectral index). A control of the inspiratory gaseous anesthetic concentrations is cascaded to the control of the EEG value in the manner of a cascade circuit. This has the advantage that a metering device (6) belonging to the arrangement meters a gaseous anesthetic mixture directly according to the patient's needs. As an alternative, the control of the numerical value is performed on the basis of an evaluation of the expiratory gaseous anesthetic concentrations resolved for individual breaths at the Y-piece (19) of the respiration circuit (12) by a gaseous anesthetic sensor (8a), preferably an infrared optical gas sensor.

20 Claims, 2 Drawing Sheets

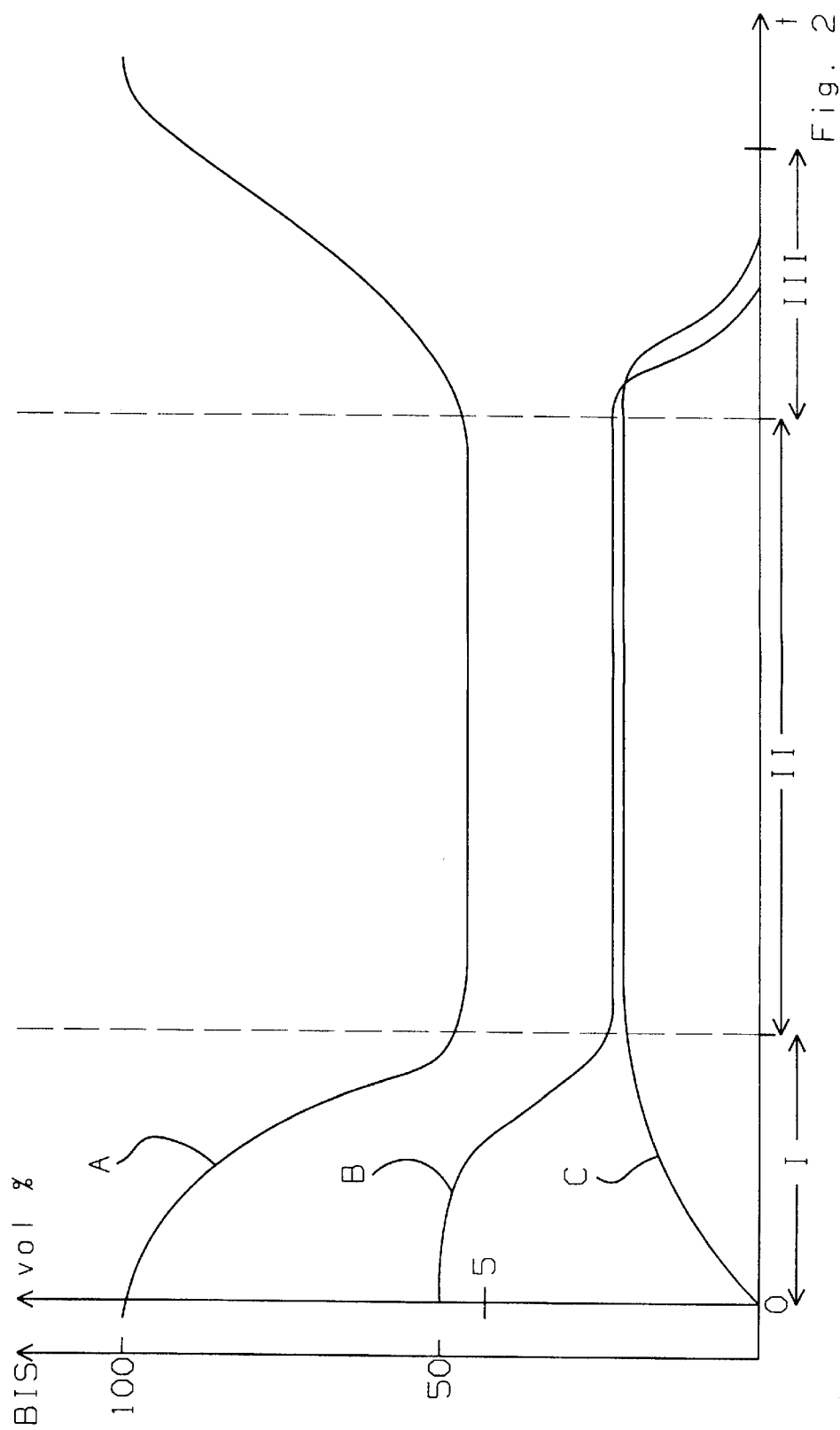

ARRANGEMENT AND PROCESS FOR CONTROLLING A NUMERICAL VALUE FOR PATIENT RESPIRATION

FIELD OF THE INVENTION

The present invention pertains to an arrangement with a control circuit for controlling a numerical value for patient respiration as well as to the control of the numerical value.

BACKGROUND OF THE INVENTION

The control of the flow of a flowing medium, especially a gas, by means of valves via a cascade control circuit is described in EP 483 401 B1. It can be used for the respiration of humans and animals for the valve-controlled supply and removal of a gaseous anesthetic. The control parameter of the first control circuit is the flow, and the position of the valves or the current and the voltage for actuating the valves may be the control parameters of the second control circuit.

A device and a process for the automation of peripheral anesthesia, which are based on measured values determined on the patient, have been known from EP 236 513 A1. The metering of anesthetics is preferably controlled there on the basis of an electromyelogram by means of electrodes distributed locally on the patient. However, the anesthetic is administered by local infusion rather than via a respiration circuit. The additional recording of an electroencephalogram of the patient is used for monitoring in order to prevent unconsciousness of the patient, which is undesirable in the case of peripheral anesthesia.

An anesthesia apparatus of this type with breathing circuit and control circuits for components of the gaseous anesthetic is described in DE 40 04 034 C2. System parameters of the breathing circuit are determined there from the changes in the concentrations of the gaseous anesthetic over time and setting parameters for the anesthetic controller are calculated from these. The changes in the concentration of a gaseous anesthetic over time in the breathing circuit depend, e.g., on the amount of the gaseous anesthetic component flowing in, the volume of the breathing circuit and the gas circulation within the breathing circuit. Due to a need-adapted adjustment of the settling parameters, which are calculated from the changes in the concentration over time, the controller furnishes time-optimized setting values. The drawback of this and other prior-art anesthesia respirators is that the control of the gaseous anesthetic components is performed only on the basis of the system parameters of the breathing circuit. As a result, the control is complicated and slow, it requires frequent calibration and is not adapted to the individual patient.

SUMMARY AND OBJECTS OF THE INVENTION

The object of the present invention is to make an arrangement for controlling a numerical value for patient respiration and a process for controlling the numerical value simpler and more rapid and at the same time to make possible a need-adapted adjustment for the respiration of the individual patient.

According to the invention an arrangement with a control circuit for controlling a numerical value for patient respiration is provided. The arrangement has a respiration circuit for delivering a gaseous anesthetic mixture to the lungs of a patient connected thereto via a Y-piece. A unit for EEG control is provided with an EEG sensor connected to the brain of the patient via head electrodes for measuring an EEG actual value, a EEG set point transducer for sending an EEG set point, an EEG comparison point, which forms the difference between the EEG actual value and the EEG set point, and an EEG controller. The controller forms a manipulated variable from the difference for a metering device for at least one anesthetic in the gaseous anesthetic mixture, so that when the EEG set point is exceeded by the EEG actual value, the percentage of at least one anesthetic in the gaseous anesthetic mixture is increased by the metering device. When the EEG actual value drops below the EEG set point, the percentage of at least one anesthetic in the gaseous anesthetic mixture is reduced by the metering device until the EEG actual value and the EEG set point agree.

The control circuit for controlling the inspiratory gaseous anesthetic concentrations may be cascaded to the control circuit for controlling the numerical value. The EEG controller forms a set point for a gaseous anesthetic comparison point, to which the inspiratory gaseous anesthetic concentrations determined by a gaseous anesthetic sensor are sent as the actual value and which forms the difference between the actual value and the set point, from the difference between the EEG actual value and the EEG set point instead of forming the manipulated variable for the metering device and for a gaseous anesthetic controller, which generates a manipulated variable for the metering device from the difference.

The arrangement may have a changeover switch that either switches on the unit for the EEG control with the cascaded control circuit for controlling the inspiratory gaseous anesthetic concentrations and switches off a unit for controlling the expiratory gaseous anesthetic concentrations or switches off the unit for the EEG control with the cascaded control circuit for controlling the inspiratory gaseous anesthetic concentrations and switches on the unit for controlling the expiratory gaseous anesthetic concentrations when no EEG actual value of the EEG sensor is available over a predetermined time period. The unit for controlling the expiratory gaseous anesthetic concentrations comprises the gaseous anesthetic sensor for measuring an actual value of the expiratory gaseous anesthetic concentrations, a gaseous anesthetic set point transducer for sending a set point for the expiratory gaseous anesthetic concentrations, a gaseous anesthetic comparison point, which forms the difference between the actual value and the set point, and a gaseous anesthetic controller, which forms a manipulated variable from the difference for the metering device, so that when the actual value drops below the set point, the percentage of at least one anesthetic in the gaseous anesthetic mixture is increased by the metering device and when the set point is exceeded by the actual value, the percentage of at least one anesthetic in the gaseous anesthetic mixture is reduced by the metering device until the actual value and the set point agree.

The control circuit for controlling a numerical value may be switched off and a corresponding gaseous anesthetic mixture may be metered into the respiration circuit, presetting inspiratory gaseous anesthetic concentrations via the metering device, when the values of the EEG or of the expiratory gaseous anesthetic concentrations are outside predetermined tolerance ranges.

The gaseous anesthetic sensors may be infrared optical gas sensors.

According to another aspect of the invention, a process is provided in which an EEG actual value is measured by a EEG sensor. An EEG set point is sent by a EEG set point transducer. The difference is formed at a EEG comparison point from the EEG actual value and the EEG set point. A manipulated variable is generated from the difference by a EEG controller for a metering device for at least one anesthetic in the gaseous anesthetic mixture so that when the EEG set point is exceeded by the EEG actual value, the percentage of at least one anesthetic in the gaseous anesthetic mixture is increased by the metering device and when the EEG actual value drops below the EEG set point, the percentage of at least one anesthetic in the gaseous anesthetic mixture is reduced by the metering device until the EEG actual value and the EEG set point agree.

According to another aspect of the invention, an arrangement is provided with a control circuit for controlling a numerical value for patient respiration. The arrangement includes a respiration circuit for delivering a gaseous anesthetic mixture to the lungs of a patient connected thereto via a Y-piece. A unit for controlling a physiological parameter of the patient includes a sensor for measuring an actual value of the physiological parameter of the patient, a set point transducer for the physiological parameter of the patient for sending a set point for the physiological parameter of the patient, a comparison point for the physiological parameter of the patient, which forms the difference between the actual value of the physiological parameter of the patient and the set point of the physiological parameter of the patient, and a controller for the physiological parameter of the patient. The controller forms from the difference a manipulated variable for the metering means for at least one anesthetic in the gaseous anesthetic mixture. When the set point of the physiological parameter of the patient is exceeded by the actual value of the physiological parameter of the patient, the percentage of at least one anesthetic in the gaseous anesthetic mixture is increased by the metering means, and when the actual value of the physiological parameter of the patient drops below the set point of the physiological parameter of the patient, the percentage of at least one anesthetic in the gaseous anesthetic mixture is reduced by the metering means until the actual value of the physiological parameter of the patient and the set point of the physiological parameter of the patient agree.

The advantage of the present invention is that a gaseous anesthetic mixture can be metered for the patient directly according to the patient's needs with a control circuit for controlling a numerical value on the basis of the evaluation of the EEG (electroencephalogram).

In a preferred embodiment, a control circuit for controlling the inspiratory gaseous anesthetic concentration in the manner of a cascade circuit is cascaded to the control circuit for controlling the numerical value. An especially rapid control of the numerical value is thus made possible.

If the EEG needed for controlling the numerical value, preferably the BIS (bispectral index), is not available over a certain time period, switching over to a control circuit for controlling the numerical value on the basis of the expiratory gaseous anesthetic concentration is possible in another advantageous embodiment of the present invention.

If the control of the numerical value cannot be performed reliably either on the basis of the EEG or on the basis of the expiratory gaseous anesthetic concentration, a safety precaution is taken according to the present invention in such a way that the gaseous anesthetic mixture is metered at an inspiratory gaseous anesthetic concentration preset automatically or by the user while all control circuits are switched off.

Besides the control of a numerical value on the basis of an evaluation of the EEG at the patient, the evaluation of other physiological parameters of the patient is also conceivable. A control circuit for controlling the inspiratory gaseous anesthetic concentration in the manner of a cascade circuit may also be cascaded to a control circuit for controlling a numerical value on the basis of the evaluation of another physiological parameter of the patient.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 2 is a graph showing the changes in BIS and the corresponding expiratory and inspiratory gaseous anesthetic concentrations over time based on the example of the gaseous anesthetic sevoflurane during an anesthesia.

DESCRIPTION OF THE PREFERRED EMBODIMENTS

Figure 1:
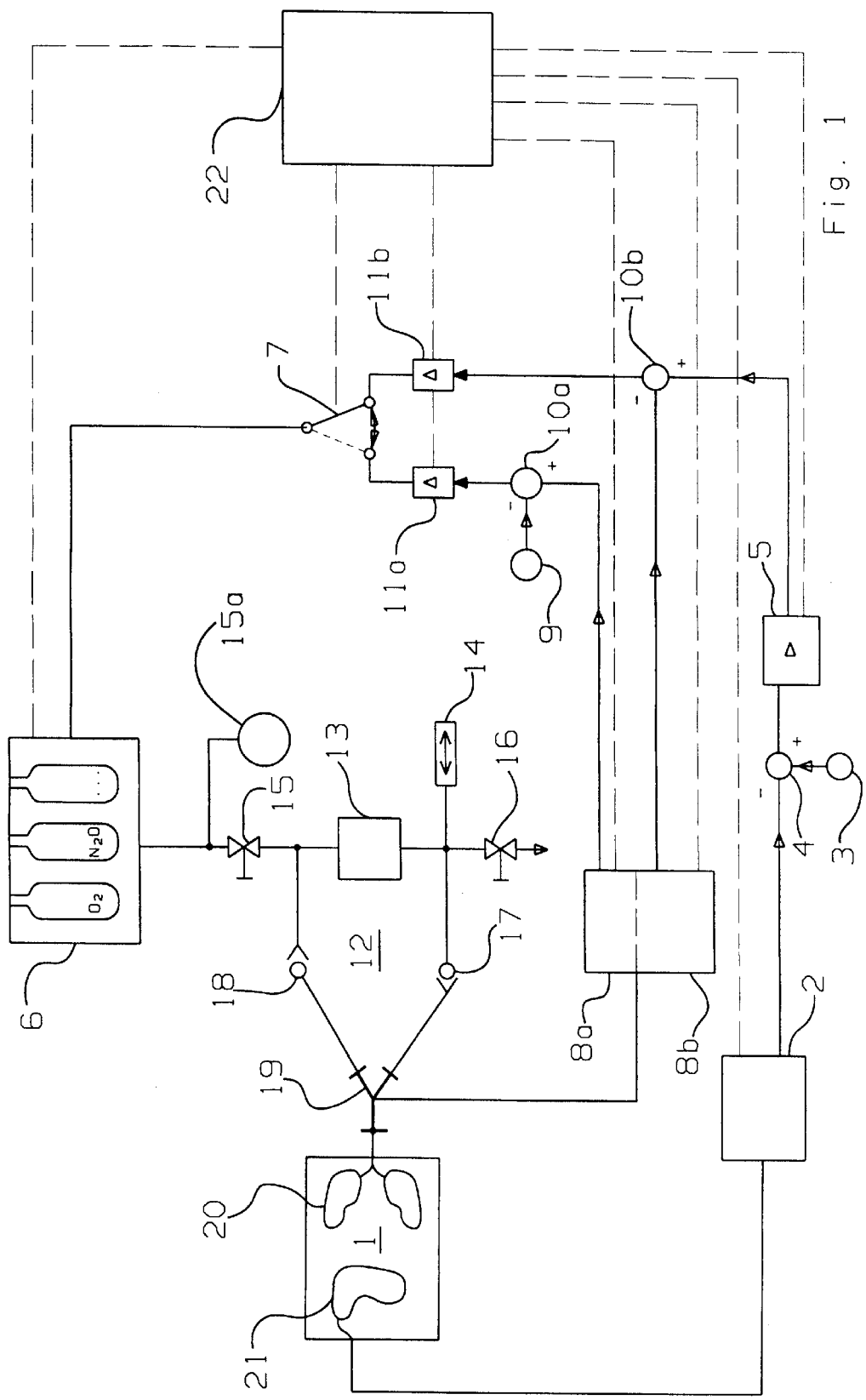
FIG. 1 is a diagram showing an arrangement for controlling a numerical value for patient respiration.

Referring to the drawings in particular, the arrangement for controlling the numerical value, which is shown in FIG. 1, comprises a respiration circuit 12, a metering device 6 for the gaseous anesthetic mixture, a unit for EEG control (electroencephalogram control), a unit for controlling the expiratory gaseous anesthetic concentrations, a changeover switch 7, which switches on either the unit for EEG control and switches off the unit for controlling the expiratory gaseous anesthetic concentrations or switches on the unit for controlling the expiratory gaseous anesthetic concentration and switches off the unit for EEG control, and a control unit 22.

The respiration circuit 12 ensures the delivery of the gaseous anesthetic mixture to the lungs 20 of a patient 1 connected thereto via the Y-piece 19. The respiratory circuit 12 is composed of a volume shift unit 14 for the respiration drive, a carbon dioxide absorber 13 for removing the carbon dioxide exhaled by the patient 1, nonreturn valves 17 and 18 for controlling the direction of the breathing gas in the respiration circuit 12, a fresh gas inlet valve 15, and an excess gas release valve 16. The breathing bag 15a is used as a manual respiration bag and as a storage device for the gas reserve in the respiration circuit 12.

The metering device 6 is used to meter the various breathing gases, gaseous anesthetics and liquid anesthetics, which together form the gaseous anesthetic mixture. The liquid anesthetic evaporates and mixes with the breathing gases and gaseous anesthetics still before the gaseous anesthetic mixture is fed into the respiration circuit 12. However, it is also conceivable as an alternative to inject liquid anesthetic directly into the respiration circuit 12 and to evaporate it there.

The unit for EEG control comprises an EEG sensor 2 connected via head electrodes to the brain 21 of the patient 1, an EEG set point transducer 3, an EEG comparison point 4, and an EEG controller 5.

A control circuit for controlling the inspiratory gaseous anesthetic concentrations in the manner of a cascade circuit is subordinated to the control circuit for controlling the EEG value, which includes the EEG control. The subordinated control circuit comprises a gaseous anesthetic sensor 8b, which measures the inspiratory concentrations in the gaseous anesthetic mixture at the Y-piece 19 via a suction line, a gaseous anesthetic comparison point 10b, and a gaseous anesthetic controller 11b.

The unit for controlling the expiratory gaseous anesthetic concentrations comprises a gaseous anesthetic sensor 8a, which measures the expiratory concentrations in the gaseous anesthetic mixture at the Y-piece 19 via a suction line, a gaseous anesthetic set point transducer 9, a gaseous anesthetic comparison point 10a, and a gaseous anesthetic controller 11a.

Infrared optical sensors are preferably used as gaseous anesthetic sensors 8a and 8b. The use of beam splitters and filters for different wavelengths of the infrared optical light makes possible the simultaneous evaluation of the different components of the gaseous anesthetic mixture. Measurement of the concentrations in the gaseous anesthetic mixture resolved for the individual breath, especially a separate measurement of the inspiratory and expiratory gaseous anesthetic concentrations by the same infrared optical sensor, is possible with the infrared optical sensors.

The arrangement for controlling the numerical value has a changeover switch 7, with which the unit for the EEG control can be switched on, as is shown in FIG. 1, and the unit for controlling the expiratory gaseous anesthetic concentrations can be switched on, or, if the changeover switch 7 is thrown, which is not shown in FIG. 1, the unit for the EEG control can be switched off and the unit for controlling the expiratory gaseous anesthetic concentrations can be switched on.

A control unit 22 with integrated microprocessor is connected to the EEG sensor 2, the EEG controller 5, the gaseous anesthetic sensors 8a and 8b, the gaseous anesthetic controllers 11a and 11b, the changeover switch 7, and the metering device 6. The position of the changeover switch 7 according to FIG. 1 shall first be assumed for the explanation of the operation of the arrangement. A corresponding numerical value is measured with the EEG sensor 2 on the basis of the EEG of the patient 1, e.g., according to a bispectral method. The value determined by the EEG sensor 2 is sent to the EEG comparison point 4 as an EEG actual value. Via the EEG set point transducer 3, the user presets a desired numerical value, which is sent to the EEG comparison point 4 as an EEG set point. The difference between the EEG actual value and the EEG set point is formed at the EEG comparison point 4, and the EEG controller 5 forms a set point for the gaseous anesthetic comparison point 10b from this difference. The inspiratory gaseous anesthetic concentrations determined by the gaseous anesthetic sensor 8b are sent as the actual value to the gaseous anesthetic comparison point 10b. The difference between the actual value and the set point is formed at the gaseous anesthetic comparison point 10b, and the gaseous anesthetic controller 11b generates a manipulated variable for the metering device 6 from this difference. If, e.g., the BIS (bispectral index), which equals 100 when the patient is wide awake and zero in deep anesthesia of the patient, is selected as the numerical value, the consequence of this is that when the BIS set point is exceeded by the BIS actual value, the percentage of certain gaseous anesthetics or anesthetics in the gaseous anesthetic mixture is increased by the metering device 6 and when the BIS actual value is lower than the BIS set point, the percentage of these gaseous anesthetics or anesthetics in the gaseous anesthetic mixture is reduced by the metering device 6.

The components in the gaseous anesthetic mixture which are metered by the metering device 6 are varied by the EEG controller 5 and the gaseous anesthetic controller 11b until the numerical value corresponds to the value desired by the user. A closed control circuit is thus obtained for the numerical value by varying a gaseous anesthetic mixture and evaluating an EEG of the patient 1.

As was described above, a control circuit for the inspiratory gaseous anesthetic concentrations is cascaded to the control circuit for controlling the EEG value. As a result, high speed of control is guaranteed for the EEG value and it is ensured, in addition, that certain upper limits of the inspiratory gaseous anesthetic concentrations will not be exceeded for the safety of the patient 1. These upper limits may be set by the user. When the upper limits are reached, an alarm is triggered. A possible upper limit for anesthetics would be, e.g., 3 to 4 times the MAC value (Minimal Alveolar Concentration) of the patient 1.

The inspiratory gaseous anesthetic concentrations are measured with the gaseous anesthetic sensor 8b at the Y-piece 19 and the expiratory gaseous anesthetic concentrations are measured with the gaseous anesthetic sensor 8a. It should be generally noted that as is known, the expiratory gaseous anesthetic concentrations are used to evaluate the effect of anesthesia in patients. The values of the expiratory gaseous anesthetic concentrations are closely correlated with the alveolar gaseous anesthetic concentration and thus also with the partial pressures of the anesthetics in the blood. The effect of the anesthesia in the brain 21 of the patient 1 can in turn be inferred from these.

Based on this relationship, both the values of the expiratory gaseous anesthetic concentrations and the corresponding EEG values of the patient 1 can be used to determine the effect of the anesthesia in a patient 1.

This is utilized in the arrangement according to the present invention by the changeover switch 7 switching off the unit for controlling the EEG and switching on the unit for controlling the expiratory gaseous anesthetic concentrations when the EEG actual value determined by the EEG sensor 2 is not available over a period longer than a preset time period, e.g., 20 sec. The numerical value for the patient respiration is controlled in this case on the basis of the expiratory gaseous anesthetic concentrations.

For example, the value that becomes established simultaneously with the EEG value during a stable phase of the patient 1 may now be used as the set point for the expiratory gaseous anesthetic concentrations.

If the unit for controlling the expiratory gaseous anesthetic concentrations is switched on by the changed position of the changeover switch 7 (not shown in FIG. 1), the value determined by the gaseous anesthetic sensor 8a for the expiratory gaseous anesthetic concentrations is sent as an actual value to the gaseous anesthetic comparison point 10a. Via the gaseous anesthetic set point transducer 9, the user presets the desired expiratory gaseous anesthetic concentrations, which are sent as a set point to the gaseous anesthetic comparison point 10a. The difference between the actual value and the set point is formed at the gaseous anesthetic comparison point 10a, and the gaseous anesthetic controller 11a generates a manipulated variable for the metering device 6 from this difference. When the set point is exceeded by the actual value, the percentage of certain gaseous anesthetics or anesthetics in the gaseous anesthetic mixture is correspondingly reduced by the metering device 6, and when the actual value is lower than the set point, the percentage of these gaseous anesthetics or anesthetics in the gaseous anesthetic is correspondingly increased by the metering device 6.

The percentages of the gaseous anesthetic mixture which are metered by the metering device 6 are varied by the gaseous anesthetic controller 11a until the expiratory gaseous anesthetic concentrations correspond to the value desired by the user. Thus, a second closed control circuit for evaluating the expiratory gaseous anesthetic concentrations at the Y-piece 19 of the respiration circuit 12 for the patient 1 is obtained as an alternative to the closed control circuit mentioned in the introduction for a numerical value for the patient respiration by varying a gaseous anesthetic mixture and evaluating an EEG of the patient 1 with a cascaded control circuit for the inspiratory gaseous anesthetic concentrations.

A switchover from the control of the numerical value for patient respiration based on the evaluation of an EEG to the control of the numerical value for patient respiration based on the evaluation of the expiratory gaseous anesthetic concentrations proved to be advantageous when EEG values are temporarily unavailable. This may have various causes, e.g., moving of the patient 1 by the medical personnel, or additional sources of electromagnetic radiation, e.g., due to the use of electrosurgical instruments and lasers. It is advisable in these cases to control the numerical value for patient respiration by evaluating the expiratory gaseous anesthetic concentrations.

It is advantageous in this connection that the determination of EEG values and the determination of the values of the expiratory gaseous anesthetic concentrations are performed completely independently from one another. Thus, mutual influence or interference of the two methods is not to be feared, and the switchover from the control of a numerical value for patient respiration based on the evaluation of an EEG to the control of the numerical value for patient respiration based on the evaluation of the expiratory gaseous anesthetic concentrations is possible if EEG values are temporarily unavailable.

As was mentioned above, a corresponding EEG value is also to be expected in the patient 1 at certain values of the expiratory gaseous anesthetic concentrations, so that the two values usually lead to corresponding information on the effect of anesthesia on the patient 1. If the evaluation of the expiratory gaseous anesthetic concentrations and the evaluation of the EEG lead to conflicting information on the effect of anesthesia on the patient 1, an alarm is triggered, or all control circuits are switched off and a corresponding gaseous anesthetic mixture is admitted into the respiration circuit 12 by presetting inspiratory gaseous anesthetic concentrations via the metering device 6. This possibility is an additional safety precaution in the arrangement for controlling the numerical value for patient respiration. Cases in which the effect of the anesthesia as determined on the basis of EEG values does not agree with the effect of anesthesia as determined on the basis of the values of the expiratory gaseous anesthetic concentrations may occur, e.g., if the patient has a cardiac pacemaker, when an electromyelogram or an electrocardiogram are simultaneously recorded in the patient 1, or the patient 1 is connected to a heart-lung machine. It is advantageous in this connection that the user can switch off the control circuits for controlling the numerical value of the patient respiration and can preset inspiratory gaseous anesthetic concentrations.

FIG. 2 shows as an example the changes in BIS (bispectral index) A over time based on the EEG of a patient 1 in the corresponding expiratory gaseous anesthetic concentration C and the inspiratory gaseous anesthetic concentration B for the gaseous anesthetic sevoflurane during anesthesia on a patient 1.

The anesthesia consists of a 10-minute induction phase I, the main phase II of the stabilized state of the patient and the 10-minute final phase III.

With the patient I awake, BIS A is between 90 and 100. For a set point of BIS A of 50, e.g., during the main phase II of a surgery, the gaseous anesthetic controller 11b generates a manipulated variable for the metering device such that the inspiratory sevoflurane concentration B measured at the Y-piece 19 is approx. 6 vol. %, corresponding to a value of 3 MAC (Minimal Alveolar Concentration) in the alveoli of the lungs 20 of the patient 1.

After a few minutes, during the induction phase I, the BIS drops to the set point 50. The expiratory sevoflurane concentration C, likewise measured at the Y-piece 19, increases during this time to a value of about 2 vol. %. The inspiratory sevoflurane concentration B is gradually reduced via the control unit 22 to a value of 2 vol. % to 2.5 vol. %.

BIS A is maintained at an approximately constant value of 50 during the main phase II of the surgery after the 10-minute induction phase I. The inspiratory sevoflurane concentration B now varies with an amplitude of 0.5 vol. % around the value that is between 2 vol. % and 2.5 vol. %. The expiratory sevoflurane concentration C varies by 0.2 vol. % around the value of about 2 vol. %.

During the 10-minute final phase III of the anesthesia, the set point for BIS A is 100; the sevoflurane metering is stopped by the metering device 6 immediately via the control unit 22. The inspiratory sevoflurane concentration B decreases, depending on the fresh gas supply, to less than 0.5 vol. % in a few minutes. The larger the amount of fresh gas supplied, the more rapidly the inspiratory sevoflurane concentration will decrease.

The expiratory sevoflurane concentration C decreases markedly more slowly, depending on the inspiratory sevoflurane concentration B and the patient-specific properties, e.g., the patient's body weight. At an expiratory sevoflurane concentration C of less than 0.5 vol. %, BIS A increases to values above 70 and the patient 1 wakes up.

Before actuating the changeover switch 7 to switch off the unit for the EEG control and switching on the unit for controlling the expiratory gaseous anesthetic concentrations, a stable phase of the patient 1 must have been established. The actual value of BIS A must be between 45 and 55. The expiratory sevoflurane concentration C must have become established at a stable value. This is the case if the expiratory sevoflurane concentration C changes by less than 0.2 vol. % within 3 minutes with the inspiratory sevoflurane concentration B maintained at a constant level. When the patient 1 is in a stable phase, the expiratory sevoflurane concentrations C corresponding to BIS A are continuously averaged over 1 minute and stored by the control unit 22. If BIS A then ceases to be able to be determined, e.g., due to movement of the patient 1 or disturbances caused by devices, the control unit 22 activates the changeover switch 7, which switches off the unit for the EEG control and switches on the unit for controlling the expiratory gaseous anesthetic concentrations. The last averaged value of the expiratory sevoflurane concentration C is then used as the set point for the gaseous anesthetic set point transducer 9. If the BIS A is again available, the changeover switch 7 will again switch on the unit for the EEG control and switch off the unit for controlling the expiratory gaseous anesthetic concentrations.

As was mentioned already in connection with FIG. 1, safety precautions, e.g., the triggering of an alarm, are taken for the case in which the inspiratory sevoflurane concentration B reaches a preset upper limit or the evaluation of the expiratory sevoflurane concentration C and the evaluation of BIS A lead to conflicting information on the effect of the anesthesia in the patient 1. The following two examples are presented for this:

EXAMPLE 1

At the beginning of the anesthesia, the upper limit for the inspiratory sevoflurane concentration B is set at 6 vol. % automatically or by presetting by the user. The set point of BIS A is still far from being reached after 3 minutes, i.e., BIS A is still between 45 and 55. However, the inspiratory sevoflurane concentration B is at the upper limit of 6 vol. % and cannot be increased any further. An alarm is triggered by the control unit 22.

EXAMPLE 2

The set point of 50 is reached by BIS A. There are corresponding value pairs for BIS A and the expiratory sevoflurane concentration C. Even though no disturbances can be recognized, one of the two values moves out of the permissible tolerance range. This is 45 to 55 for BIS A and, e.g., 1.8 vol. % to 2.6 vol. % for the expiratory sevoflurane concentration. An alarm is triggered by the control unit 22.

While specific embodiments of the invention have been shown and described in detail to illustrate the application of the principles of the invention, it will be understood that the invention may be embodied otherwise without departing from such principles.

What is claimed is:

1. A patient respiration numerical value control circuit arrangement comprising:

a respiration circuit with a Y-piece for delivering a gaseous anesthetic mixture to the lungs of a patient;

a metering device for metering at least one anesthetic in the gaseous anesthetic mixture;

an electroencephalogram (EEG) control with an EEG sensor adapted to be connected to the brain of the patient via head electrodes for measuring an EEG actual value, a EEG set point transducer for sending an EEG set point, an EEG comparison point, which forms the difference between the EEG actual value and the EEG set point, and a EEG controller, which forms a manipulated variable from the difference for the metering device so that when the EEG set point is exceeded by the EEG actual value, the percentage of at least one anesthetic in the gaseous anesthetic mixture is increased by the metering device and when the EEG actual value drops below the EEG set point, the percentage of at least one anesthetic in the gaseous anesthetic mixture is reduced by the metering device until the EEG actual value and the EEG set point agree.

2. An arrangement in accordance with claim 1, wherein a control circuit for controlling the inspiratory gaseous anesthetic concentrations is cascaded to the EEG control, wherein the EEG controller forms a set point for a gaseous anesthetic comparison point, to which the inspiratory gaseous anesthetic concentrations determined by a gaseous anesthetic sensor are sent as the actual value and which forms the difference between the actual value and the set point, from the difference between the EEG actual value and the EEG set point instead of forming the manipulated variable for the metering device, and a gaseous anesthetic controller, which generates a manipulated variable for the metering device from the difference.

3. An arrangement in accordance with claim 2, further comprising a changeover switch, which either switches on the unit for the EEG control with the cascaded control circuit for controlling the inspiratory gaseous anesthetic concentrations and switches off a unit for controlling the expiratory gaseous anesthetic concentrations or switches off the unit for the EEG control with the cascaded control circuit for controlling the inspiratory gaseous anesthetic concentrations and switches on the unit for controlling the expiratory gaseous anesthetic concentrations when no EEG actual value of the EEG sensor is available over a predetermined time period, wherein the unit for controlling the expiratory gaseous anesthetic concentrations comprises a gaseous anesthetic sensor for measuring an actual value of the expiratory gaseous anesthetic concentrations, a gaseous anesthetic set point transducer for sending a set point for the expiratory gaseous anesthetic concentrations, a gaseous anesthetic comparison point, which forms the difference between the actual value and the set point, and a gaseous anesthetic controller, which forms a manipulated variable from the difference for the metering device, so that when the actual value drops below the set point, the percentage of at least one anesthetic in the gaseous anesthetic mixture is increased by the metering device and when the set point is exceeded by the actual value, the percentage of at least one anesthetic in the gaseous anesthetic mixture is reduced by the metering device until the actual value and the set point agree.

4. An arrangement in accordance with claim 3, wherein the control circuit for controlling a numerical value is switched off and a corresponding gaseous anesthetic mixture is metered into the respiration circuit, presetting inspiratory gaseous anesthetic concentrations via the metering device, when the values of the EEG or of the expiratory gaseous anesthetic concentrations are outside predetermined tolerance ranges.

5. An arrangement in accordance with claim 3, wherein the gaseous anesthetic sensors are infrared optical gas sensors.

6. A control process, comprising the steps of:

providing a metering device for metering at least one anesthetic in the gaseous anesthetic mixtures;

measuring an electroencephalogram (EEG) actual value with an EEG sensor;

sending an EEG set point from a EEG set point transducer;

forming a difference at an EEG comparison point from the EEG actual value and the EEG set point;

generating a manipulated variable with an EEG controller from the difference for controlling the metering device so that when the EEG set point is exceeded by the EEG actual value, the percentage of at least one anesthetic in the gaseous anesthetic mixture is increased by the metering device and when the EEG actual value drops below the EEG set point, the percentage of at least one anesthetic in the gaseous anesthetic mixture is reduced by the metering device until the EEG actual value and the EEG set point agree.

7. A process in accordance with claim 6, further comprising:

using a numerical value control circuit arrangement with a respiration circuit with a piece for delivering a gaseous anesthetic mixture to the lungs of a patient connected thereto, the metering device and an EEG control with an EEG sensor connected to the brain of the patient via head electrodes for measuring an EEG actual value, a EEG set point transducer for sending an EEG set point, an EEG comparison point, which forms the difference between the EEG actual value and the EEG set point, and an EEG controller.

8. A process in accordance with claim 7, further comprising:

using a control circuit for controlling the inspiratory gaseous anesthetic concentrations cascaded to the EEG control, wherein the EEG controller forms a set point for a gaseous anesthetic comparison point, to which the inspiratory gaseous anesthetic concentrations determined by a gaseous anesthetic sensor are sent as the actual value and which forms the difference between the actual value and the set point, from the difference between the EEG actual value and the EEG set point instead of forming the manipulated variable for the metering device, and a gaseous anesthetic controller, which generates a manipulated variable for the metering device from the difference.

9. A process in accordance with claim 8, further comprising:

using a changeover switch for either switching on the unit for the EEG control with the cascaded control circuit for controlling the inspiratory gaseous anesthetic concentrations and switches off a unit for controlling the expiratory gaseous anesthetic concentrations or switching off the unit for the EEG control with the cascaded control circuit for controlling the inspiratory gaseous anesthetic concentrations and switches on the unit for controlling the expiratory gaseous anesthetic concentrations when no EEG actual value of the EEG sensor is available over a predetermined time period, wherein the unit for controlling the expiratory gaseous anesthetic concentrations comprises the gaseous anesthetic sensor for measuring an actual value of the expiratory gaseous anesthetic concentrations, a gaseous anesthetic set point transducer for sending a set point for the expiratory gaseous anesthetic concentrations, a gaseous anesthetic comparison point, which forms the difference between the actual value and the set point, and a gaseous anesthetic controller, which forms a manipulated variable from the difference for the metering device, so that when the actual value drops below the set point, the percentage of at least one anesthetic in the gaseous anesthetic mixture is increased by the metering device and when the set point is exceeded by the actual value, the percentage of at least one anesthetic in the gaseous anesthetic mixture is reduced by the metering device until the actual value and the set point agree.

10. An arrangement with a control circuit for controlling a numerical value for patient respiration, the arrangement comprising:

a respiration circuit for delivering a gaseous anesthetic mixture to the lungs of a patient via a Y-piece;

a metering device for metering at least one anesthetic in the gaseous anesthetic mixture;

a unit for controlling a physiological parameter of the patient, comprising a sensor for measuring an actual value of the physiological parameter of the patient;

a set point transducer for the physiological parameter of the patient for sending a set point for the physiological parameter of the patient;

a comparison element forming a difference between the actual value of the physiological parameter of the patient and the set point of the physiological parameter of the patient;

a controller for controlling the metering device so that when the set point of the physiological parameter of the patient is exceeded by the actual value of the physiological parameter of the patient, the percentage of at least one anesthetic in the gaseous anesthetic mixture is increased by the metering device, and when the actual value of the physiological parameter of the patient drops below the set point of the physiological parameter of the patient, the percentage of at least one anesthetic in the gaseous anesthetic mixture is reduced by the metering device until the actual value of the physiological parameter of the patient and the set point of the physiological parameter of the patient agree.

11. Arrangement in accordance with claim 10, wherein a control circuit for controlling the inspiratory gaseous anesthetic concentrations is cascaded to the control circuit for controlling the numerical value, wherein the controller for the physiological parameter of the patient forms a set point for a gaseous anesthetic comparison point, to which the inspiratory gaseous anesthetic concentrations determined by a gaseous anesthetic sensor are sent as the actual value and which forms the difference between the actual value and the set point, from the difference between the actual value of the physiological parameter of the patient and the set point of the physiological parameter of the patient instead of forming the manipulated variable for the metering device, and for a gaseous anesthetic controller, which generates a manipulated variable for the metering device from the difference.

12. An arrangement in accordance with claim 10, further comprising a changeover switch, which either switches on the unit for controlling the physiological parameter of the patient with the cascaded control circuit for controlling them inspiratory gaseous anesthetic concentrations and switches off a unit for controlling the expiratory gaseous anesthetic concentrations or switches off the unit for controlling the physiological parameter of the patient with the cascaded control circuit for controlling the inspiratory gaseous anesthetic concentrations and switches on the unit for controlling the expiratory gaseous anesthetic concentrations when no actual value of the physiological parameter of the patient is available from the sensor for the physiological parameter of the patient over a preset time period, wherein the unit for controlling the expiratory gaseous anesthetic concentrations comprises a gaseous anesthetic sensor for measuring an actual value of the expiratory gaseous anesthetic concentrations, a gaseous anesthetic set point transducer for sending a set point for the expiratory gaseous anesthetic concentrations, a gaseous anesthetic comparison point, which forms the difference between the actual value and the set point, and a gaseous anesthetic controller, which forms a manipulated variable for the metering device, so that when the actual value drops below the set point, the percentage of at least one anesthetic in the gaseous anesthetic mixture is increased by the metering device and when the set point is exceeded by the actual value, the percentage of at least one anesthetic in the gaseous anesthetic mixture is reduced by the metering device until the actual value and the set point agree.

13. An arrangement in accordance with claim 12, wherein the control circuit for controlling a numerical value is switched off and a corresponding gaseous anesthetic mixture is metered into the respiration circuit, presetting inspiratory gaseous anesthetic concentrations, when the values of the physiological parameter of the patient or of the expiratory gaseous anesthetic concentrations are outside preset tolerance ranges.

14. An arrangement in accordance with claim 12, wherein the gaseous anesthetic sensors are infrared optical gas sensors.

15. A process for controlling a numerical value, the process comprising:
   measuring an actual value of a physiological parameter of the patient with a sensor for the physiological parameter of the patient;
   sending a set point of the physiological parameter of the patient with a set point transducer for the physiological parameter of the patient;
   forming the difference between the actual value of the physiological parameter of the patient and the set point of the physiological parameter of the patient at a comparison point for the physiological parameter of the patient; and
   generating a manipulated variable from the difference by a controller of the physiological parameter of the patient for controlling the metering device including:
      increasing a percentage of at least one anesthetic in the gaseous anesthetic mixture when the set point of the physiological parameter of the patient is exceeded by the actual value of the physiological parameter of the patient; and
      reducing the percentage of at least one anesthetic in the gaseous anesthetic mixture when the actual value of the physiological parameter of the patient drops below the set point of the physiological parameter of the patient until the actual value of the physiological parameter of the patient and the set point of the physiological parameter of the patient agree.

16. A process in accordance with claim 15, further comprising the step of:
   using a numerical value control circuit arrangement with a respiration circuit with a Y-piece for delivering a gaseous anesthetic mixture to the lungs of a patient connected thereto, the metering device and an EEG control with an EEG sensor connected to the brain of the patient via head electrodes for measuring an EEG actual value, a EEG set point transducer for sending an EEG set point, an EEG comparison point, which forms the difference between the EEG actual value and the EEG set point, and an EEG controller.

17. A process in accordance with claim 16, further comprising:
   using a control circuit for controlling the inspiratory gaseous anesthetic concentrations cascaded to the EEG control, wherein the EEG controller forms a set point for a gaseous anesthetic comparison point, to which the inspiratory gaseous anesthetic concentrations determined by a gaseous anesthetic sensor are sent as the actual value and which forms the difference between the actual value and the set point, from the difference between the EEG actual value and the EEG set point instead of forming the manipulated variable for the metering device, and a gaseous anesthetic controller, which generates a manipulated variable for the metering device from the difference.

18. A process in accordance with claim 17, further comprising:
   using a changeover switch for either switching on the unit for the EEG control with the cascaded control circuit for controlling the inspiratory gaseous anesthetic concentrations and switches off a unit for controlling the expiratory gaseous anesthetic concentrations or switching off the unit for the EEG control with the cascaded control circuit for controlling the inspiratory gaseous anesthetic concentrations and switches on the unit for controlling the expiratory gaseous anesthetic concentrations when no EEG actual value of the EEG sensor is available over a predetermined time period, wherein the unit for controlling the expiratory gaseous anesthetic concentrations comprises the gaseous anesthetic sensor for measuring an actual value of the expiratory gaseous anesthetic concentrations, a gaseous anesthetic set point transducer for sending a set point for the expiratory gaseous anesthetic concentrations, a gaseous anesthetic comparison point, which forms the difference between the actual value and the set point, and a gaseous anesthetic controller, which forms a manipulated variable from the difference for the metering device, so that when the actual value drops below the set point, the percentage of at least one anesthetic in the gaseous anesthetic mixture is increased by the metering device and when the set point is exceeded by the actual value, the percentage of at least one anesthetic in the gaseous anesthetic mixture is reduced by the metering device until the actual value and the set point agree.

19. A process for controlling anesthetic to a patient, the process comprising the steps of:
   providing a set physiological point for a physiological parameter of the patient;
   measuring an actual physiological value of a physiological parameter of the patient;
   calculating a physiological difference between said set physiological point and said actual physiological value;
   creating an anesthetic set point based on said physiological difference;
   delivering anesthetic to the patient;
   measuring an anesthetic concentration to form an anesthetic actual value;
   comparing said anesthetic actual value with said anesthetic set point;
   controlling the anesthetic to the patient to cause said anesthetic actual value to be substantially equal to said anesthetic set point.

20. A process in accordance with claim 19, wherein:
   said anesthetic actual value, is an inspiratory anesthetic actual value;
   said anesthetic set point is an inspiratory anesthetic set point;
   said controlling is a physiological controlling;
   an expiratory controlling is also provided, said expiratory controlling including;
      measuring the anesthetic exhaled from the patient to form an expiratory anesthetic actual value;
      providing an expiratory anesthetic set point;
      comparing said expiratory anesthetic actual value with said expiratory anesthetic set point;
      expiratory controlling the anesthetic to the patient to cause said expiratory anesthetic actual value to be substantially equal to said expiratory anesthetic set point;
   the process of controlling the anesthetic gas selectively switches between said physiological controlling and said expiratory controlling.

* * * * *